(12) United States Patent
Li et al.

(10) Patent No.: US 10,060,949 B2
(45) Date of Patent: Aug. 28, 2018

(54) PROBE DEVICE OF VERTICAL PROBE CARD

(71) Applicant: CHUNGHWA PRECISION TEST TECH. CO., LTD., Taoyuan (TW)

(72) Inventors: Wen Tsung Li, Taoyuan (TW); Kai Chieh Hsieh, Taoyuan (TW)

(73) Assignee: CHUNGHWA PRECISION TEST TECH. CO., LTD., Taoyuan (TW)

( * ) Notice: Subject to any disclaimer, the term of this patent is extended or adjusted under 35 U.S.C. 154(b) by 0 days.

(21) Appl. No.: 15/435,309

(22) Filed: Feb. 17, 2017

(65) Prior Publication Data

US 2018/0059140 A1 Mar. 1, 2018

(30) Foreign Application Priority Data

Aug. 24, 2016 (TW) .............................. 105127133 A

(51) Int. Cl.
| | | |
|---|---|---|
| *G01R 31/00* | (2006.01) | |
| *G01R 1/073* | (2006.01) | |
| *G01R 1/04* | (2006.01) | |
| *G01N 1/00* | (2006.01) | |
| *G01R 1/00* | (2006.01) | |

(52) U.S. Cl.
CPC ....... *G01R 1/07371* (2013.01); *G01R 1/0416* (2013.01); *G01N 1/00* (2013.01); *G01R 1/00* (2013.01); *H01L 2221/00* (2013.01)

(58) Field of Classification Search
CPC ....... G01R 1/00; H01L 21/00; H01L 2221/00; C12Q 1/00; C12Q 2304/00; G01N 1/00; G01N 2201/00
See application file for complete search history.

(56) References Cited

U.S. PATENT DOCUMENTS

| | | | | |
|---|---|---|---|---|
| 4,423,376 A * | 12/1983 | Byrnes | ................... | G01R 1/073 324/750.25 |
| 4,506,215 A * | 3/1985 | Coughlin | ............... | G01R 1/073 324/72.5 |
| 4,535,536 A * | 8/1985 | Wyss | ................. | G01R 1/07371 29/845 |
| 4,622,514 A * | 11/1986 | Lewis | ................ | G01R 1/07357 324/72.5 |

(Continued)

FOREIGN PATENT DOCUMENTS

| | | |
|---|---|---|
| JP | 2001183392 A | 7/2001 |
| TW | 200301360 A | 7/2003 |

(Continued)

*Primary Examiner* — Jermele M Hollington
*Assistant Examiner* — Temilade Rhodes-Vivour
(74) *Attorney, Agent, or Firm* — JMB Davis Ben-David

(57) ABSTRACT

A probe device of a vertical probe card is provided and includes a die assembly and at least one pin assembly. The die assembly includes a first die, a second die, and a middle die disposed between the first die and the second die. The at least one pin assembly has a first pin, a second pin, and at least one electrical connector. The at least one electrical connector is connected to the first pin and the second pin. The at least one pin assembly is electrically contacted with at least one contact pad of a device under test. The at least one contact pad leans against the at least one pin assembly, so that the at least one pin assembly generates a deformation in a longitudinal direction.

13 Claims, 4 Drawing Sheets

(56) References Cited

U.S. PATENT DOCUMENTS

| | | | | |
|---|---|---|---|---|
| 4,633,176 A | * | 12/1986 | Reimer | ............ G01R 1/07371 |
| | | | | 324/750.25 |
| 4,899,104 A | | 2/1990 | Luther | |
| 6,292,003 B1 | * | 9/2001 | Fredrickson | ......... G01R 1/0483 |
| | | | | 324/750.25 |
| 2017/0059615 A1 | * | 3/2017 | Hsieh | ................ G01R 1/07371 |
| 2017/0082656 A1 | * | 3/2017 | Chen | ................ G01R 1/06722 |

FOREIGN PATENT DOCUMENTS

| | | | |
|---|---|---|---|
| TW | 200730845 A | | 8/2007 |
| TW | 200829921 A | | 7/2008 |

\* cited by examiner

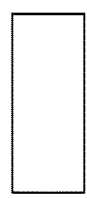 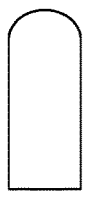 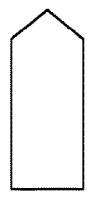 
FIG. 5A   FIG. 5B   FIG. 5C   FIG. 5D
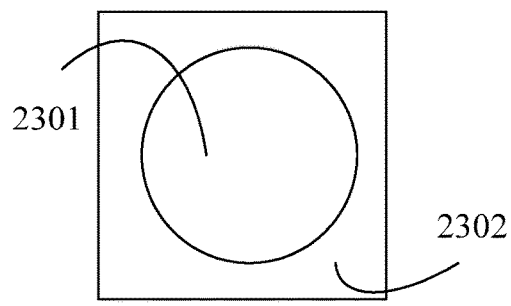
FIG. 6

PROBE DEVICE OF VERTICAL PROBE CARD

CROSS-REFERENCE TO RELATED APPLICATIONS

Benefit is claimed to Taiwan Patent Application No. 105127133, filed Aug. 24, 2016; the contents of which are incorporated by reference herein in their entirety.

BACKGROUND OF THE INVENTION

Field of Invention

The present invention relates to a probe device, and more particularly to a probe device utilized for a vertical probe card.

Description of Prior Art

In recent years, with the development of precision and multifunction of electronic products, chip structures of integrated circuits in the electronic products are more complicated as well. In a manufacturing process, chips are usually produced in massive batches. Accordingly, in order to ensure electrical performance of the chips, chip-level tests are required before the chips are packaged.

In a conventional manufacturing process of the chips, probe cards are usually used for testing the chips. The probe cards can be classified into cantilever probe cards and vertical probe cards. When a probe card is used, pins of the probe card are in electrical contact with contact pads of the chips firstly. Then, a circuit board assembly of the probe card is electrically connected to a tester. The tester transmits test signals to the chips or receives output signals from the chips, thereby achieving effect of measuring electrical performance of the chips. Moreover, a user can weed out chips with defects for the following package process.

Please refer to FIG. 1, which shows a vertical probe card 100 in the prior art. The vertical probe card 100 includes a circuit board assembly 110 and a probe device. The probe device includes a die assembly 120 and a plurality of pins 130. One terminal of each of the pins 130 is electrically connected to a contact pad 51' (e.g., a metal pad, a metal bump, a solder ball, and so on) of the circuit board assembly 110, and the other terminal of each of the pins 130 passes through the die assembly 120 and is electrically connected to a corresponding contact pad 51 of a device under test 50. Specifically, the die assembly 120 includes a first die 121 (usually referred to as an upper die) and a second die 123 (usually referred to as a lower die). Plural upper openings 122 penetrate vertically through the first die 121. Plural lower openings 124 penetrate vertically through the second die 123. The upper openings 122 are disposed corresponding to the lower openings 124, so that each of the pins 130 can pass through a corresponding one of the upper openings 122 and a corresponding one of the lower openings 124. Furthermore, the die assembly 120 further includes a spacer element 129. The spacer element 129 fixes the first die 121 and the second die 123 and maintains a longitudinal distance between the first die 121 and the second die 123, so that a needle arrangement space is formed in the die assembly 120. As a result, when the vertical probe card 100 is electrically contacted with the contact pads 51 of the device under test 50, elastic deformation of the pins 130 can absorb reversed stress during a test. That is, the needle arrangement space of the die assembly 120 serves as an elastic deformation space of the pins 130.

However, when the pins 130 are elastically deformed in the needle arrangement space of the die assembly 120, the vertical probe card 100 has a short circuit because two adjacent ones of the pins 130 are easily electrically contacted with each other.

As shown in FIG. 1, cobra needles, which are pre-bent, are used as pins 130 of the vertical probe card 100 in the prior art. Since probe overdrive is generated through a shape of the pins 130, a transmission path is relatively long. Furthermore, the pins 130 have a poor conductivity due to this pre-bent processing method.

In another vertical probe card in the prior art, microelectromechanical systems (MEMS) needles are used. That is, the pins are manufactured by a MEMS manufacturing process. Although a structure of the pins is straight, the pins have to be assembled to be tilted, so that actuation overdrive of the pins can be formed as an elastic structure. The pins are made of metal to improve physical characteristics. For example, the pins are usually made of an alloy (a copper alloy or a nickel alloy). Accordingly, a resistivity is relatively high, and an electrical conductivity is poor. A length of the overdrive of the pins is limited as well even if the pins are collocated with any other structure.

As mentioned above, the pins in the prior art cannot be moved straight up and down (in a vertical direction), so that force in a horizontal direction is generated and destroys a surface of the at least one contact pad 51 to generate probing marks. Preferably, it is better that the probing marks have a small area and a shallow depth. Production yield is decreased in the following package process when the probe marks have a large area or a great depth.

Consequently, there is a need to provide an improved vertical probe card to solve the above-mentioned problems in the prior art.

SUMMARY OF THE INVENTION

To solve the above-mentioned technical problems, an objective of the present invention is to provide a probe device of a vertical probe card in which a composited pin including a conductive metal and a structural metal replaces a conventional pin. The inner conductive metal provides a low resistivity when signals are transmitted. The outer structural metal provides rigidity and oxidation resistance. In a conventional manufacturing process of print circuit boards, the present invention can reduce production cost when compared to MEMS technology.

To achieve the above-mentioned objective, the present invention provides a probe device of a vertical probe card comprising: a die assembly, comprising: a first die having at least one upper opening which penetrates vertically through the first die; a second die having at least one lower opening which penetrates vertically through the second die, and the at least one lower opening being disposed corresponding to the at least one upper opening; and a middle die disposed between the first die and the second die and having at least one middle opening which penetrates vertically through the middle die; and at least one pin assembly having a first pin, a second pin, and at least one electrical connector, wherein the at least one electrical connector is connected to the first pin and the second pin, the at least one pin assembly is inserted in the die assembly and passes through the at least one upper opening, the at least one middle opening, and the at least one lower opening, the at least one pin assembly is electrically contacted with at least one contact pad of a device under test, the at least one contact pad leans against the at least one pin assembly, so that the at least one pin assembly generates a deformation in a longitudinal direction, which is perpendicular to a surface of the at least one contact pad of the device under test.

In one preferred embodiment of the present invention, a center line of the at least one upper opening is shifted by a horizontal distance with respect to a center line of the at least one lower opening and a center line of the at least one middle opening. When the at least one contact pad leans against the at least one pin assembly, the at least one electrical connector is deformed to change a length of the at least one pin assembly in the longitudinal direction.

In one preferred embodiment of the present invention, only one pin is disposed in each of the at least one upper opening, the at least one lower opening, and at least one middle opening.

In one preferred embodiment of the present invention, a top part of the at least one pin assembly includes a plane, a round shape, a tip shape, or a claw shape.

In one preferred embodiment of the present invention, a ratio of a longitudinal length of the at least one electrical connector to a horizontal length of the at least one electrical connector is ranged from 3:1 to 1:1.

In one preferred embodiment of the present invention, a ratio of a longitudinal length of the at least one electrical connector to a horizontal length of the at least one electrical connector is ranged from 2:1 to 1:1.

In one preferred embodiment of the present invention, the die assembly further comprises a spacer element disposed between the first die and the middle die and between the middle die and the second die, and the spacer element fixes the first die and the middle die and fixes the middle die and the second die. The spacer element maintains a first longitudinal distance between the first die and the middle die and maintains a second longitudinal distance between the middle die and the second die to form a needle arrangement space in the die assembly.

In one preferred embodiment of the present invention, the first die further comprises at least one fixed opening for aligning to at least one fixed element disposed in the middle die, and the at least one fixed element is used for fixing the middle die and the spacer element.

In one preferred embodiment of the present invention, the first pin passes through the first die, the second pin passes through the middle die and the second die, and an insulating layer is disposed on at least one of the first pin between the middle die and the first die and the second pin between the middle die and the first die.

In one preferred embodiment of the present invention, the first pin, the second pin, and the at least one electrical connector are formed integrally together.

In one preferred embodiment of the present invention, the first pin, the second pin, and the at least one electrical connector comprise a conductive metal and a structural metal which coats the conductive metal.

In one preferred embodiment of the present invention, a metal complex is formed between the conductive metal and the structural metal.

In one preferred embodiment of the present invention, the metal complex is formed after an annealing process is performed to the conductive metal and the structural metal.

BRIEF DESCRIPTION OF THE DRAWINGS

FIG. 5A to FIG. 5D show enlarged schematic diagrams of a top part S1 of one of the pin assemblies in FIG. 2.

FIG. 6 shows a sectional view of one of the pin assemblies in FIG. 2.

DETAILED DESCRIPTION OF THE PREFERRED EMBODIMENTS

To make the above-mentioned objectives, features, and advantages of the present invention more clearly and definitely, the present invention will be described in details below by using preferred embodiments in conjunction with the appending drawings.

Figure 1:
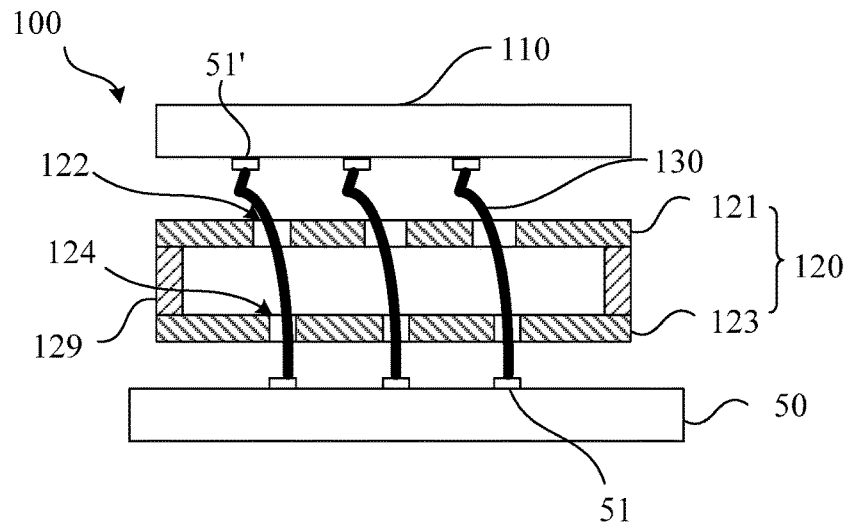
FIG. 1 shows a vertical probe card in the prior art.
Figure 2:
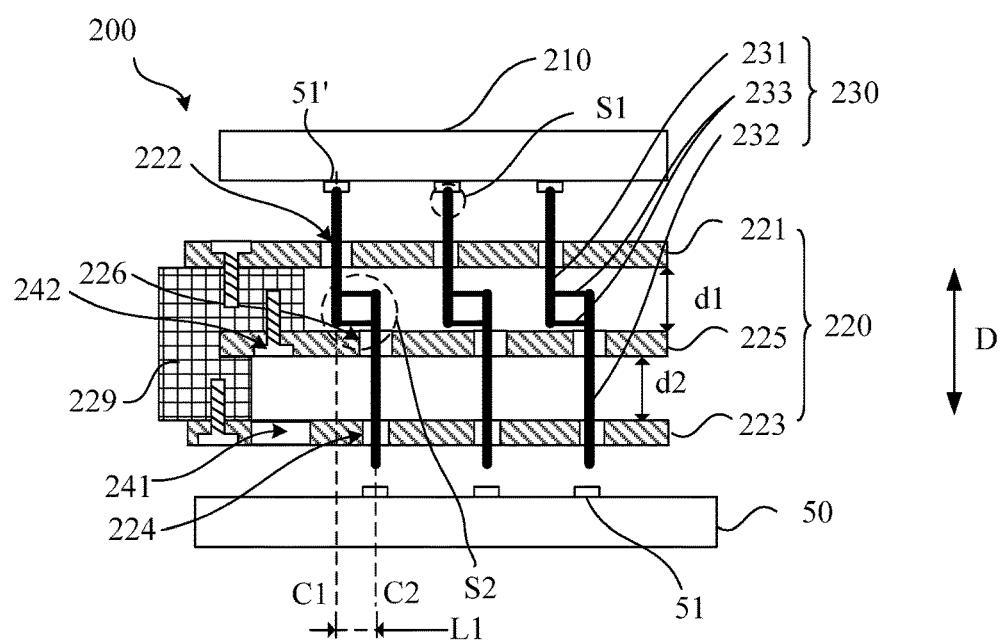
FIG. 2 shows a structural diagram of a vertical probe card in accordance with a first preferred embodiment of the present invention.

Please refer to FIG. 2. FIG. 2 shows a structural diagram of a vertical probe card 200 in accordance with a first preferred embodiment of the present invention. The vertical probe card 200 includes a printed circuit assembly 210 and a probe device. The probe device includes a die assembly 220 and a plurality of pin assemblies 230. Each of the pin assemblies 230 includes a first pin 231, a second pin 232, and at least one electrical connector 233. The at least one electrical connector 233 is connected to the first pin 231 and the second pin 232. One terminal of each of the pin assemblies 230 is electrically connected to one contact pad 51' (e.g., a metal pad, a metal bump, a solder ball, and so on) of the circuit board assembly 210. The other terminal of each of the pin assemblies 230 passes through the die assembly 220 and is electrically contacted with a corresponding contact pad 51 of a device under test (hereinafter referred to as DUT) 50 outside the vertical probe card 200. Each of the pin assemblies 230 and the corresponding contact pad 51 lean against each other, so that each of the pin assemblies 230 generates a deformation in a longitudinal direction D. Accordingly, the pin assemblies 230 can move straight up and down, and a situation that a surface of the at least one contact pad 51 is destroyed due to contacts can be decreased. It is noted that the longitudinal direction D is perpendicular to the surface of the at least one contact pad 51 of the DUT 50. Specifically, when the at least one contact pad 51 leans against the one of the pin assemblies 230, the at least one electrical connector 233 is deformed to change a length of the one of the pin assemblies 230 in the longitudinal direction D. In one embodiment, a deformation of the at least one electrical connector 233 in a horizontal direction is designed to be far less than the deformation in the longitudinal direction D, so that the deformation of the one of the pin assemblies 230 focuses on the longitudinal direction D to decrease a displacement of the second pin 232 in the horizontal direction.

When the vertical probe card 200 is used, the pin assemblies 230 of the vertical probe card 200 are electrically contacted with the corresponding contact pads 51 (e.g., metal pads, metal bumps, solder balls, and so on) of the DUT 50 (e.g., a chip). Then, the pin assemblies 230 are vertically electrically contacted with the corresponding contact pads 51. The circuit board assembly 210 of the vertical probe card 200 is electrically connected to a tester (not shown). The tester transmits test signals to the DUT 50 or receives output signals from the DUT 50, thereby achieving effect of measuring electrical characteristics of the DUT 50. Furthermore, a user can weed out chips with defects for the following package process.

As shown in FIG. 2, the die assembly 220 includes a first die 221 (usually referred to as an upper die), a middle die 225, and a second die 223 (usually referred to as a lower die). Plural upper openings 222 penetrate vertically through the first die 221. Plural middle openings 226 penetrate vertically through the middle die 225. Plural lower openings 224 and at least one fixed opening 241 penetrate vertically through the lower die 223. A function of the at least one fixed opening 241 will be described later. The upper openings 222, the middle openings 226, and the lower openings 224 are disposed correspondingly. Accordingly, each of the probe assemblies 230 passes through a corresponding one of the upper openings 222, a corresponding one of the middle openings 226, and a corresponding one of the lower openings 224, and each of the probe assemblies 230 is electrically contacted with a corresponding one of the contact pads 51 of the DUT 50. As shown in FIG. 2, a first center line C1 (i.e., a center line of each of the upper openings 222) is shifted by a horizontal distance L1 with respect to a second center line C2 (i.e., a center line of each of the lower openings 224 and a center line of each of the middle openings 226). When the contact pads 51' lean against the pin assemblies 230, the at least one electrical connector 233 is deformed, so that the length of each of the pin assemblies 230 is changed in the longitudinal direction D. It is noted that only one pin is allowed to be disposed in each of the upper openings 222, each of the middle openings 226, and each of the lower openings 224. That is, each of the openings does not include more than one pin disposed therein, thereby avoiding that two adjacent pins are electrically contacted with each other. Further, it is better for the second pins 232 to be moved up and down (longitudinally) only and not to be moved horizontally, as far as possible. This is mainly because the present invention uses the at least one electrical connector 233 which may be deformed easily. Accordingly, the deformation occurs at the at least one electrical connector 233.

Specifically, the second center line C2 of each of the lower openings 224 is shifted by the horizontal distance L1 with respect to the first center line C1.

As shown in FIG. 2, the die assembly 220 further includes a spacer element 229. The spacer element 229 fixes the first die 221 and the middle die 225 and fixes the middle die 225 and the second die 223. The spacer element 229 maintains a longitudinal distance d1 between the first die 221 and the middle die 225 and maintains a longitudinal distance d2 between the middle die 225 and the second die 223. Accordingly, a needle arrangement space is formed in the die assembly 220. The at least one fixed opening 241 is used for aligning to at least one fixed element 242 disposed in the middle die 225. The at least one fixed element 242 is used for fixing the middle die 225 and the spacer element 229. In the present invention, assembling difficulty of the vertical probe card 200 can be significantly reduced by disposing the at least one fixed opening 241. Furthermore, the at least one fixed element 242 is fixed according to different demands, so as to control a distance between the middle die 225 and the second die 223. Specifically, the first pins 231 pass through the first die 221. The second pins 232 pass through the middle die 225 and the second die 223. Preferably, the middle die 225 can lean against the first pins 231 of the pin assemblies 230 due to the at least one fixed element 242. In other words, the middle die 225 fixes the first pins 231, so that only the at least one electrical connector 233 and the second pins 232 of the pin assemblies 230 can be moved. Specifically, the first pins 231 are fixed without being moved. The second pins 232 are moved only along the longitudinal direction D. The at least one electrical connector 233 is the only one element which can be deformed.

It is noted that the at least one fixed element 242 and other fixed elements disposed in the first die 221 and the second die 223 are respectively embedded to be flush with a surface of the first die 221, a surface of the second die 223, and a surface of the middle die 225. Accordingly, stress can be resisted when the pin assemblies 230 are deformed, thereby avoiding that the vertical probe card 200 is deformed or damaged.

Figure 3:
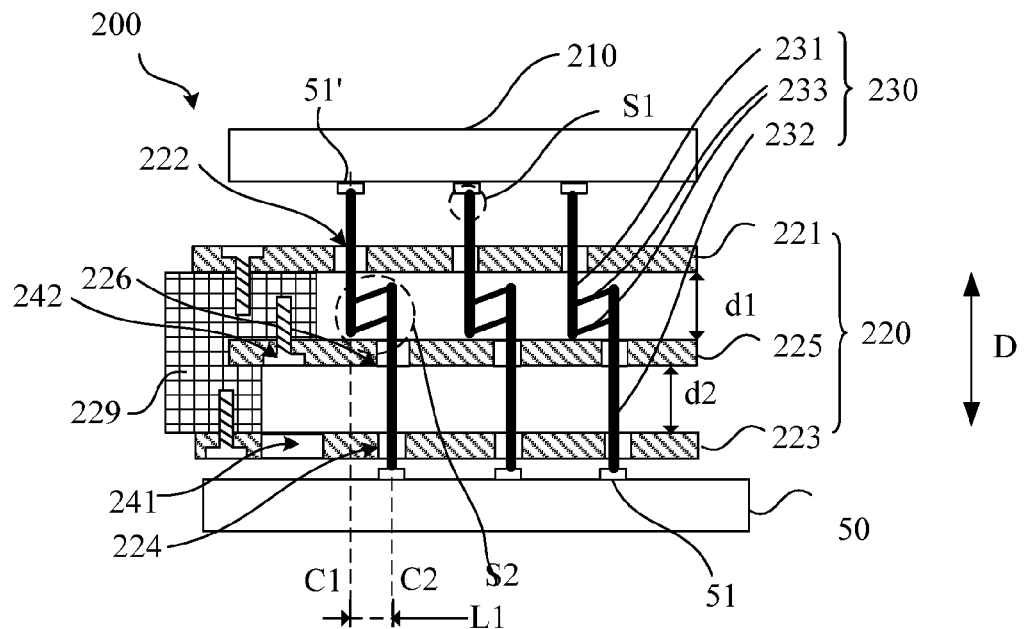
FIG. 3 shows that one electrical connector is deformed.

Please refer to FIG. 3, which shows that the at least one electrical connector 233 is deformed. When the contact pads 51' lean against the first pins 231 in an operating process, the second pins 232 are moved up and drive the at least one electrical connector 233 to be deformed in the longitudinal direction D. As a result, a situation that surfaces of the contact pads 51 are destroyed due to contacts can be decreased.

Figure 4:
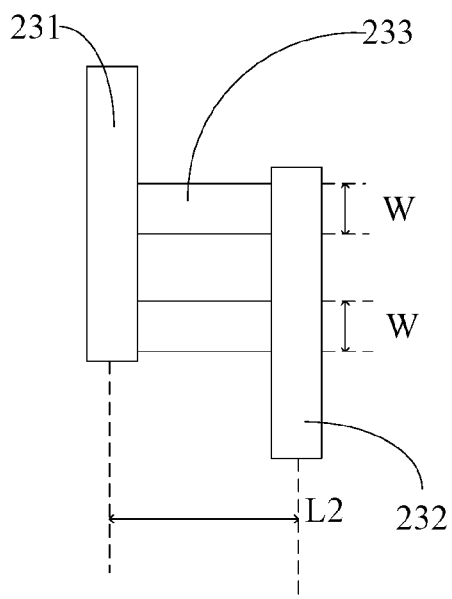
FIG. 4 shows an enlarged schematic diagram of a main deformation area S2 of one of the pin assemblies in FIG. 2.

Please refer to FIG. 4, which shows an enlarged schematic diagram of a main deformation area S2 of one of the pin assemblies 230 in FIG. 2. In the present preferred embodiment, each of the pin assemblies 230 includes two electrical connectors 233. However, according to different demands, a number of the electrical connectors 233 can be increased to bear a higher test current. Further, according to required test stress, a longitudinal length W (parallel with the first pins 231 and the second pins 232) can be adjusted, or the number of the electrical connectors 233 can be increased. Alternatively, a horizontal length L2 of each of the electrical connectors 233 can be adjusted according to a distance between two adjacent ones of the contact pads 51. It is noted that better test effect can be acquired when a ratio of the longitudinal length W of each of the electrical connectors 233 to the horizontal length L2 of each of the electrical connectors 233 is 1 to 3. Preferably, the ratio of the longitudinal length W of each of the electrical connectors 233 to the horizontal length L2 of each of the electrical connectors 233 is 2.

FIG. 5A to FIG. 5D show enlarged schematic diagrams of a top part S1 of one of the pin assemblies 230 in FIG. 2. Since the die assembly 220 of the vertical probe card 200 in accordance with the present invention includes the middle die 225 disposed therein, all of the pin assemblies 230 inserted in the die assembly 220 can be separated effectively. Accordingly, in the vertical probe card 200 in accordance with the present invention, an insulating coating step of the pin assemblies 230 is not required. Furthermore, the pin assemblies 230 need not be formed as a specific shape via a secondary processing. As a result, production steps can be simplified effectively, and production cost can be reduced. That is, as shown in FIG. 5A to FIG. 5D, the pin assemblies 230 in the present invention can be formed as basic geometric shapes by using a simpler processing method. For example, the top part of each of the pin assemblies 230 may include a plane (as shown in FIG. 5A) or a polygon (e.g., a round shape as shown in FIG. 5B, a tip shape as shown in FIG. 5C, or a claw shape as shown in FIG. 5D). In the same manner, in any other preferred embodiment of the present invention, pins of a vertical probe card may be formed as basic geometric shapes by using a simpler processing method, thereby reducing the production cost.

Please refer to FIG. 6, which shows a sectional view of one of the pin assemblies 230 in FIG. 2. The first pin 231, the second pin 232, and the electrical connector 233 include a conductive metal 2301 and a structural metal 2302 which coats the conductive metal 2301. Generally, the conductive metal 2301 is made of copper. However, rigidity and oxidation resistance of the copper are poor, and thus the structural metal 2302 is used for improving the rigidity and the oxidation resistance. Compared to the prior art in which an alloy is used, the pins in accordance with the present invention can bear a current higher than 350 milliamperes (mA). However, in order to avoid that the conductive metal 2301 and the structural metal 2302 are separated from each other, preferably, an annealing process is used for generating a metal complex between the conductive metal 2301 and the structural metal 2302, thereby enhancing an adhesive force between the conductive metal 2301 and the structural metal 2302. In FIG. 6, the conductive metal 2301 is cylindrical and then coated by the structural metal 2302. In practical applications, the conductive metal 2301 may be a copper wire, a copper plate, or a copper strip. Shapes of the conductive metal 2301 and the structural metal 2302 are not limited thereto.

Specifically, the first pin 231, the second pin 232, and the at least one electrical connector 233 of each of the pin assemblies 230 are formed integrally together. In other words, the conductive metal 2301 is formed as the first pin 231, the second pin 232, and the at least one electrical connector 233 of each of the pin assemblies 230 first. Then, the structural metal 2302 is deposited on the first pin 231, the second pin 232, and the at least one electrical connector 233 to cover the first pin 231, the second pin 232, and the at least one electrical connector 233.

Figure 7:
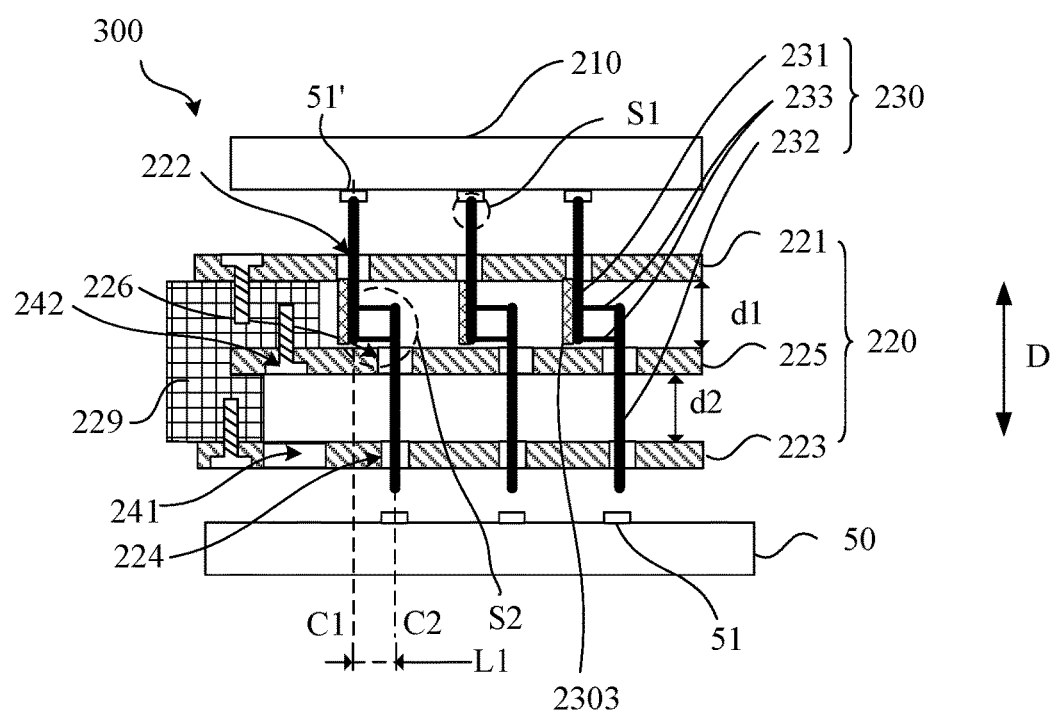
FIG. 7 shows a structural diagram of a vertical probe card in accordance with a second preferred embodiment of the present invention.

FIG. 7 shows a structural diagram of a vertical probe card 300 in accordance with a second preferred embodiment of the present invention. A difference between the present preferred embodiment and the first preferred embodiment is that the vertical probe card 300 further includes an insulating layer 2303 disposed on each of the first pins 231 between the middle die 225 and the first die 221. In FIG. 7, the insulating layer 2303 is disposed on only one side of each of the pin assemblies 230. In practical operations, the insulating layer 2303 may cover each of the first pins 231 between the middle die 225 and the first die 221 according to different demands. The insulating layer 2303 is used for preventing any one of the pin assemblies 230 from being contacted with an adjacent one of the pin assemblies 230 when the pin assemblies 230 are deformed.

In any other preferred embodiment, the insulating layer 2303 may be optionally disposed on each of the second pins 232 between the middle die 225 and the first die 221. Alternatively, the insulating layer 2303 is disposed on each of the first pins 231 between the middle die 225 and the first die 221 and disposed on each of the second pins 232 between the middle die 225 and the first die 221.

As is understood by a person skilled in the art, the foregoing preferred embodiments of the present invention are illustrative rather than limiting of the present invention. It is intended that they cover various modifications and similar arrangements be included within the spirit and scope of the present invention, the scope of which should be accorded the broadest interpretation so as to encompass all such modifications and similar structures.

What is claimed is:

1. A probe device of a vertical probe card, comprising:
a die assembly, comprising:
a first die having at least one upper opening which penetrates vertically through the first die;
a second die having at least one lower opening which penetrates vertically through the second die, and the at least one lower opening being disposed corresponding to the at least one upper opening; and
a middle die disposed between the first die and the second die and having at least one middle opening which penetrates vertically through the middle die; and
at least one pin assembly having a first pin, a second pin, and at least one electrical connector,
wherein the at least one electrical connector is connected to the first pin and the second pin, the at least one pin assembly is inserted in the die assembly and passes through the at least one upper opening, the at least one middle opening, and the at least one lower opening, the at least one pin assembly is electrically contacted with at least one contact pad of a device under test, the at least one contact pad leans against the at least one pin assembly, so that the at least one pin assembly generates a deformation in a longitudinal direction, which is perpendicular to a surface of the at least one contact pad of the device under test,
wherein the second pin of the at least one pin assembly is capable of being moved straight up and down in the longitudinal direction.

2. The probe device of the vertical probe card of claim 1, wherein a center line of the at least one upper opening is shifted by a horizontal distance with respect to a center line of the at least one lower opening and a center line of the at least one middle opening,
when the at least one contact pad leans against the at least one pin assembly, the at least one electrical connector is deformed to change a length of the at least one pin assembly in the longitudinal direction.

3. The probe device of the vertical probe card of claim 1, wherein only one pin is disposed in each of the at least one upper opening, the at least one lower opening, and at least one middle opening.

4. The probe device of the vertical probe card of claim 1, wherein a top part of the at least one pin assembly includes a plane, a round shape, a tip shape, or a claw shape.

5. The probe device of the vertical probe card of claim 1, wherein a ratio of a longitudinal length of the at least one electrical connector to a horizontal length of the at least one electrical connector is ranged from 3:1 to 1:1.

6. The probe device of the vertical probe card of claim 1, wherein a ratio of a longitudinal length of the at least one electrical connector to a horizontal length of the at least one electrical connector is ranged from 2:1 to 1:1.

7. The probe device of the vertical probe card of claim 1, wherein the die assembly further comprises a spacer element disposed between the first die and the middle die and between the middle die and the second die, and the spacer element fixes the first die and the middle die and fixes the middle die and the second die,
the spacer element maintains a first longitudinal distance between the first die and the middle die and maintains a second longitudinal distance between the middle die and the second die to form a needle arrangement space in the die assembly.

8. The probe device of the vertical probe card of claim 7, wherein the first die further comprises at least one fixed opening for aligning to at least one fixed element disposed in the middle die, and the at least one fixed element is used for fixing the middle die and the spacer element.

9. The probe device of the vertical probe card of claim 1, wherein the first pin passes through the first die, the second pin passes through the middle die and the second die, and an insulating layer is disposed on at least one of the first pin between the middle die and the first die and the second pin between the middle die and the first die.

10. The probe device of the vertical probe card of claim 1, wherein the first pin, the second pin, and the at least one electrical connector are formed integrally together.

11. The probe device of the vertical probe card of claim 1, wherein the first pin, the second pin, and the at least one electrical connector comprise a conductive metal and a structural metal which coats the conductive metal.

12. The probe device of the vertical probe card of claim 11, wherein a metal complex is formed between the conductive metal and the structural metal.

13. The probe device of the vertical probe card of claim 12, wherein the metal complex is formed after an annealing process is performed to the conductive metal and the structural metal.

* * * * *